United States Patent [19]

Strehlke et al.

[11] 3,979,465
[45] Sept. 7, 1976

[54] PROCESS FOR THE PRODUCTION OF LOWER ALIPHATIC ALCOHOLS

[75] Inventors: Günter Strehlke, Rheinkamp-Baerl; Günther Osterburg, Homberg, both of Germany

[73] Assignee: Deutsche Texaco Aktiengesellschaft, Hamburg, Germany

[22] Filed: Jan. 7, 1974

[21] Appl. No.: 431,177

[30] Foreign Application Priority Data
Jan. 13, 1973 Germany............................ 2301632

[52] U.S. Cl............................. 260/639 R; 423/531
[51] Int. Cl.² ........................................ C07C 29/06
[58] Field of Search.................. 423/531; 260/639 R

[56] References Cited
UNITED STATES PATENTS

| | | | |
|---|---|---|---|
| 2,390,316 | 12/1945 | Mottern | 423/531 |
| 2,755,297 | 7/1956 | Smith et al. | 260/639 R |
| 2,808,378 | 10/1957 | Baldwin et al. | 260/639 R |
| 2,955,920 | 10/1960 | Belchetz | 423/531 |

OTHER PUBLICATIONS
Perry, *Perry Chemical Engineer's Handbook*, 4ed. (1963), section 11, pp. 28, 29.

*Primary Examiner*—Joseph E. Evans
*Attorney, Agent, or Firm*—T. H. Whaley; C. G. Ries; J. J. O'Loughlin

[57] ABSTRACT

Process for the production of an aliphatic alcohol comprising reacting an olefin having from 2 to 4 carbon atoms with sulfuric acid to form an ester reaction product, diluting said product with water and steam stripping to remove a lower aliphatic alcohol overhead leaving a dilute sulfuric acid solution, concentrating said dilute sulfuric acid solution in a first stage indirect evaporator, recycling the steam generated in this first stage evaporator to the steam stripping step, further concentrating the sulfuric acid solution in a second stage direct heat evaporator to form a concentrated sulfuric acid solution and recycling said concentrated sulfuric acid solution for reaction with fresh olefin feed.

7 Claims, 1 Drawing Figure

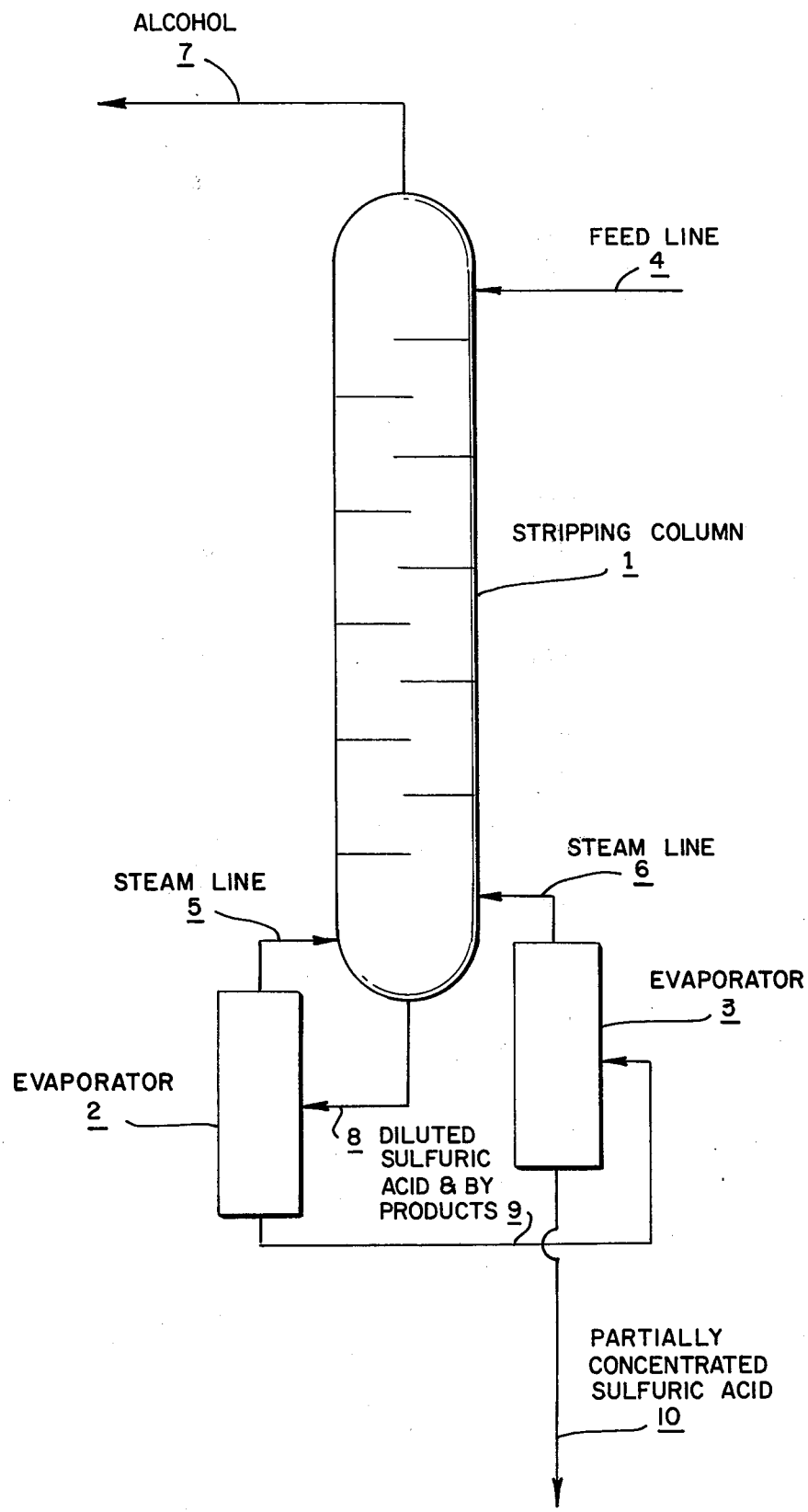

PROCESS FOR THE PRODUCTION OF LOWER ALIPHATIC ALCOHOLS

BACKGROUND OF THE INVENTION

This invention relates to an improved liquid-phase concentrated sulfuric acid process for the indirect hydrolysis of an olefin to produce a lower aliphatic alcohol.

It is known to produce a lower aliphatic alcohol by reacting the corresponding olefin with concentrated sulfuric acid to form an ester reaction product and thereafter hydrolyzing the ester reaction product to form a lower aliphatic alcohol. This process is characterized by producing large quantities of dilute sulfuric acid together with some undesirable by-products. For this process to be feasible, it is essential that the dilute sulfuric acid be purified and concentrated so that it can be recycled to the esterification reaction.

It is also known to concentrate the dilute sulfuric acid effluent from this process by means of a direct heat immersion-burner unit. In addition to concentrating the dilute sulfuric acid, the immersion-burner effects a combustion of the undesirable by-products present in the dilute sulfuric acid effluent and thus purifies the sulfuric acid being concentrated serving to facilitate the recycling of the acid to the process.

A serious draw-back to the direct heat immersion-burner concentration step is that the environment in the evaporator or concentrator is very corrosive. The effective life of the direct heat immersion-burner is unusually short under the extremely corrosive conditions prevailing. Short immersion-burner life or early failure is, therefore, a serious limitation or bottleneck in this process.

An improved process has been developed which substantially reduces the immersion-burner corrosion problem and which is more efficient in the utilization of the heat energy input.

SUMMARY OF THE INVENTION

According to this process, an aliphatic olefin having from 2 to 4 carbon atoms is reacted with concentrated sulfuric acid to form an ester reaction product of said olefin and said sulfuric acid. Water is added to the ester reaction product to promote hydrolysis of the ester reaction product. The aqueous dilute ester reaction product is introduced into a stripping column and contacted with steam to effect stripping of the aliphatic alcohol obtained from the hydrolyzed ester overhead.

Dilute sulfuric acid is withdrawn from the stripping column and introduced into a first stage evaporator employing indirect heat exchange. The steam generated in this evaporator is passed into the stripping column to effect the stripping procedure referred to above. The partially concentrated sulfuric acid is then passed into a second stage direct heat evaporator to further concentrate the sulfuric acid and to oxidize or burn off the impurities in the sulfuric acid. The so concentrated and purified sulfuric acid is recycled to the initial olefin esterification reaction.

DESCRIPTION OF THE DRAWING

Referring to the drawing, FIG. 1 is an illustration of a stripping column and first stage evaporators wherein the principal aspects of the present process are conducted.

Stripping column 1 is connected to feed line 4 through which the dilute ester reaction product is introduced into the top of the stripping column. Line 8 is connected to the bottom of the stripping column and to first stage evaporator 2 and serves to conduct the stripped and diluted sulfuric acid bottoms and by-products into the evaporator. Line 5 is a steam line connecting evaporator 2 to a low point in the stripping column. Steam generated in the evaporator 2 by indirect heat exchange (not illustrated) is passed into the stripping column via line 5 for the purpose of stripping the dilute ester reaction product feed.

Evaporator 3 is a second evaporator in the first stage evaporation step. Line 9 connects evaporator 2 to evaporator 3. Steam generated in evaporator 3 by indirect heat exchange is passed into the stripping column via connecting line 6. The partially concentrated sulfuric acid from the first stage indirect heat evaporation step is removed via line 10 and passed into a second stage direct heat evaporator not illustrated.

DETAILED DESCRIPTION OF THE INVENTION

In accordance with this process an aliphatic olefin and concentrated sulfuric acid are contacted in a suitable reaction vessel to effect a reaction and the formation of an ester of the olefin and sulfuric acid in an ester reaction product. The olefins which can be employed are the lower aliphatic olefins having from 2 to 4 carbon atoms. These will include ethylene, propylene, 1-butene and 2-butene. In general, the olefin feed mixture will contain at least about 65 percent of the desired olefin in admixture with the related saturated aliphatic hydrocarbons. It is preferred to employ an olefin feed mixture containing at least about 70 percent of olefin with the most preferred feed mixture containing greater than 80 up to 100 percent olefin. Commercial olefin feed streams will usually have from 70 to 85 percent of olefin present.

It is essential in this process to employ a concentrated sulfuric acid in the ester reaction. The sulfuric acid must have a concentration greater than 70 percent. The preferred concentration for this process is from about 73 to 80 percent sulfuric acid. The esterification reaction is conducted at a temperature ranging from about 40° to about 60°C under a pressure of from about 16 to 20 atmospheres.

Water is added to the ester reaction product to promote hydrolysis of the ester to the corresponding aliphatic alcohol and regeneration of sulfuric acid. The amount of water employed is not critical but should be a substantial excess over that needed to effect complete esterification of the ester reaction product. This process can be expedited by heating the aqueous dilute ester reaction product. Heating the ester reaction product at a temperature above about room temperature up to about 100°C is increasingly effective for promoting the hydrolysis reaction with temperatures from 50° to 100°C. being preferred.

The substantially hydrolyzed ester reaction product is introduced into the top of a stripping column while steam is introduced near the bottom of the stripping column. The aliphatic alcohol from the hydrolyzed ester is taken off overhead from the stripping column. At the same time, the dilute sulfuric acid from the hydrolysis reaction is removed from the bottom of the stripping column. This sulfuric acid solution will generally have a sulfuric acid concentration of less than about 45 percent and generally from about 35 to 45 percent.

The dilute sulfuric acid solution is conducted into a first stage evaporator employing indirect heat exchange. While any means of indirect heat exchange is effective for the first stage evaporation, steam has been found most convenient. Steam at a temperature from about 120° to 150°C under a pressure from about 2 to 10 atmospheres is highly effective as the indirect heat source in the first stage evaporator. This first stage evaporation by indirect heat exchange can be conducted using two or more evaporators. In a typical example, steam at about 125°–130°C under about 2.5 atmosphere is employed in a first evaporator and steam at 140°–150°C. under about 5 atmospheres is employed in a second evaporator.

In general, the dilute sulfuric acid which leaves the stripper column at a concentration of from 40 to 45 percent is concentrated up to a range from about 55 to 65 percent in the first stage indirect-heat evaporator. It is preferred to conduct this evaporation in one or more steps to effect a concentration in the range from about 60 to 65 percent.

The first stage evaporation is essential to the effectiveness of the present process. In the first place, the steam generated in this evaporation is employed in the stripping column for removing the lower aliphatic alcohol produced overhead. This procedure provides important overall economies in the heat input to this process amounting to about 0.8 to 1 ton of steam per ton of alcohol produced.

More importantly, effecting a major part of the concentration of the sulfuric acid in the steam evaporator employing indirect heat exchange removes a substantial evaporation load from the direct heat immersion-burner unit. This is a critical feature in the present process because of the short life of the immersion-burner in the corrosive environment prevailing. By reducing the evaporation load on the direct heat immersion-burner, the through-put or capacity of this process is increased by a factor of 2 to 2.5 which is a most surprising aspect of this process. A further significant improvement is the reduced amount of exhaust gas emissions due to the reduced use of the direct heat immersion-burner which facilitates the meeting of statutory clear air standards by this process.

The alcohols produced correspond to the olefin in the feed stream. This process is particularly suited to the production of ethyl alcohol, isopropyl alcohol and the butyl alcohols, such as sec. butyl alcohol.

The following examples further illustrate preferred embodiments of this invention.

EXAMPLE 1

PRODUCTION OF ISOPROPYL ALCOHOL (IPA)

In a pressure-proof stirring vessel, 2.1 kg per hour of a 73 percent sulfuric acid are reacted with 0.95 kg of a liquified propene-propane-mixture (ratio 85/15) at a temperature of 60°C, whereby 0.65 kg per hour of propene are absorbed so that 2.75 kg per hour of a reaction mixture of isopropyl alcohol, i-propyl sulfate, sulfuric acid, and water (thick $C_3$ ester) is yielded. 2.75 kg of the said thick $C_3$ ester are diluted with 1.1 kg of water at a temperature of 80°C and are prehydrolyzed at this temperature for 0.5 to 1 hour.

1150 grams of the resultant dilute $C_3$ ester (specific gravity at 20°C: 1.15) are passed per hour at a temperature of 80°C via line 4 to the head of stripping column 1. The 1150 grams of dilute IPA ester contain 5.5 moles of chemically combined propylene i.e., about 86 percent as free alcohol and 14 percent as sulfuric acid ester. Thus, the said dilute ester is composed of 34.5 percent of sulfuric acid, 28.8 percent of crude alcohol (including ether) and of 36.7 percent of water.

The ratio of sulfuric acid to water is 48.5 : 51.5 parts by weight.

The aqueous isopropyl alcohol is now stripped with 283 grams of steam per hour in countercurrent flow via head 7 in stripping column 1 and subsequently is condensed. Simultaneously, the sulfuric acid ester, still present in the dilute ester, is hydrolyzed to sulfuric acid and isopropyl alcohol.

The ratio of sulfuric acid to water of 48.5 : 51.5 present in the said dilute ester, is reduced to a ratio of sulfuric acid to water of 42 : 58 in the stripping column by means of the stripping process.

On account of the isopropyl alcohol being stripped off the described dilute ester, 488 grams per hour of an aqueous crude alcohol with about 67 percent by weight of isopropyl alcohol are yielded.

The 283 grams of the steam per hour required in stripping column 1 are produced in evaporators 2 and 3 by reconcentrating the alcohol-free 42 percent sulfuric acid discharged from the stripping column 1 to 60 percent.

The steam developed is passed to the stripping column via lines 5 and 6.

The reconcentration of the sulfuric acid is conducted by means of indirect addition of energy in Stage 1, 2 with a steam of 2.5 atmospheres at 127°C and in Stage 2, 3 749 grams of a 53 percent sulfuric acid is reconcentrated to 662 grams of a 60 percent sulfuric acid by evaporating 87 grams of water.

The sulfuric acid to be reconcentrated is passed to the evaporators 2 and 3 via lines 8 and 9. 662 grams of a 60 percent sulfuric acid per hour are passed via line 10 for the final reconcentration to 73 percent and for cleaning into said immersion-burner unit.

EXAMPLE 2

PRODUCTION OF SEC.-BUTYL ALCOHOL (SBA)

0.675 kg of butene are absorbed by 1.83 kg of a 75 percent sulfuric acid at 53°C from butene-butane-mixture (ratio 72/28) in a pressure proof extraction column, whereby 2.5 kg of a reaction mixture of sec.-butyl alcohol, butyl sulfate, sulfuric acid, and water (thick $C_4$ ester) are obtained, said reaction mixture being diluted with 1.5 kg of water at 80°C and prehydrolyzed at this temperature for 0.5 to 1 hour.

1 liter of the resultant dilute $C_4$ ester (specific gravity at 20°C: 1.320) is supplied per hour to the stripping column via line 4.

1320 grams of dilute SBA ester contain 3.9 mole of combined butene. About 84 percent thereof are present as free sec.-butyl alcohol whereas 16 percent are bound as sulfuric acid ester.

The ratio of sulfuric acid to water is 47.5 : 52.5 parts by weight.

The dilute ester comprises in composition 37.0 percent of sulfuric acid, 21.9 percent of crude alcohol, and 41.1 percent of water.

The aqueous sec.-butyl alcohol is stripped with 349 grams of steam per hour in stripping column 1 via head 7, thereby yielding 507 grams of aqueous crude alcohol with about 57 percent by weight of sec.butyl alcohol.

The sulfuric acid ester is hydrolyzed in the stripping column to sulfuric acid and sec.-butyl alcohol.

The ratio of sulfuric acid to water of 47.5 : 52.5 in the said dilute SBA ester is diluted by means of the stripping process to a ratio of sulfuric acid to water of 42 : 58 parts by weight.

The change in concentration in the stripping column is comparable with the one described in Example 1.

The 349 grams of steam per hour required in the stripping column are produced in the evaporators 2 and 3 by reconcentrating the discharged 42 percent sulfuric acid.

The foregoing examples illustrate the more important advantages of the novel process of the invention. Substantial overall heat energy input is reduced to the extent of 0.8 to 1 ton of steam per ton of alcohol produced by employing the steam from the first stage evaporators in the stripping column. Corrosion losses to the immersion-burner in the second stage direct heat evaporator are very significantly reduced because a major part of the required evaporation is completed in the first stage evaporator.

We claim:

1. A process for the production of a lower aliphatic alcohol comprising reacting an olefin having from 2 to 4 carbon atoms with sulfuric acid of a concentration greater than 70 percent in a reaction vessel to form an ester reaction product, adding water to said product to form a dilute ester reaction product and promote hydrolysis, steam stripping said dilute ester reaction product in a stripping column to remove a lower aliphatic alcohol overhead leaving a dilute sulfuric acid solution containing less than about 45 percent sulfuric acid, concentrating said dilute sulfuric acid solution in a first stage evaporator employing indirect heat exchange means to an intermediate solution containing from about 55 to 65 percent sulfuric acid, recycling the steam generated in the first stage evaporator to said steam stripping step, further concentrating said intermediate sulfuric acid solution in a second stage direct heat evaporator employing an immersion-burner to form a concentrated sulfuric acid solution containing at least 70 percent sulfuric acid and recycling said concentrated sulfuric acid solution to said reaction vessel.

2. A process according to claim 1 in which said dilute ester reaction product is heated at an elevated temperature up to about 100°C.

3. A process according to claim 1 in which said first stage sulfuric acid concentration is conducted in a plurality of evaporators employing indirect heat exchange.

4. A process according to claim 1 in which said lower aliphatic alcohol is ethanol and said olefin is ethylene.

5. A process according to claim 1 in which said lower aliphatic alcohol is isopropyl alcohol and said olefin is propylene.

6. A process according to claim 1 in which said lower aliphatic alcohol is secondary butyl alcohol and said olefin is 1-butene.

7. A process according to claim 1 in which said dilute sulfuric acid solution contains about 40 to 45 percent sulfuric acid and said first stage evaporation employing indirect heat exchange is conducted in two steps, employing steam at about 125° to 130°C under about 2.5 atmospheres in the first step and steam at about 140° to 150°C under about 5 atmospheres in the second step to produce an intermediate solution containing about 55 to 65 percent sulfuric acid and further concentrating said intermediate sulfuric acid solution in said second stage evaporator to form a concentrated sulfuric acid solution containing above about 70 percent sulfuric acid.

* * * * *